United States Patent
Sutton et al.

(10) Patent No.: US 12,011,315 B2
(45) Date of Patent: Jun. 18, 2024

(54) INTRACRANIAL BLOOD PRESSURE ESTIMATION METHOD AND DEVICE

(71) Applicant: KONINKLIJKE PHILIPS N.V., Eindhoven (NL)

(72) Inventors: Jonathan Thomas Sutton, Boston, MA (US); Raghavendra Srinivasa Naidu, Auburndale, MA (US); Shyam Bharat, Arlington, MA (US); Jonathan Fincke, Belmont, MA (US); Balasundar Iyyavu Raju, North Andover, MA (US); Shriram Sethuraman, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 319 days.

(21) Appl. No.: 17/602,888

(22) PCT Filed: Apr. 2, 2020

(86) PCT No.: PCT/EP2020/059332
§ 371 (c)(1),
(2) Date: Oct. 11, 2021

(87) PCT Pub. No.: WO2020/207883
PCT Pub. Date: Oct. 15, 2020

(65) Prior Publication Data
US 2022/0160327 A1 May 26, 2022

Related U.S. Application Data

(60) Provisional application No. 62/832,077, filed on Apr. 10, 2019.

(51) Int. Cl.
*A61B 8/04* (2006.01)
*A61B 8/00* (2006.01)
(Continued)

(52) U.S. Cl.
CPC .......... *A61B 8/04* (2013.01); *A61B 8/06* (2013.01); *A61B 8/461* (2013.01); *A61B 8/488* (2013.01)

(58) Field of Classification Search
CPC .. A61B 8/04; A61B 8/06; A61B 8/461; A61B 8/488
See application file for complete search history.

(56) References Cited

U.S. PATENT DOCUMENTS

| 5,997,479 A | 12/1999 | Savord |
| 6,013,032 A | 1/2000 | Savord |

(Continued)

FOREIGN PATENT DOCUMENTS

WO 2004107963 A2 12/2004

OTHER PUBLICATIONS

International Search Report and Written Opinion, International Application No. PCT/EP2020/059332, dated Jul. 9, 2020.
(Continued)

*Primary Examiner* — Rochelle D Turchen

(57) ABSTRACT

A method (20) and device for deriving an estimate of intracranial blood pressure based on motion data for a wall of an intracranial blood vessel, intracranial blood flow velocity, and a blood pressure signal measured at a location outside the brain. The method is based on identifying (28) a time offset between the two intracranial signals (vessel wall movement and vessel blood flow), and then applying (30) this offset to the blood pressure signal acquired from outside the brain to obtain a fourth signal, indicative of estimated intracranial blood pressure.

20 Claims, 5 Drawing Sheets

(51) Int. Cl.
*A61B 8/06* (2006.01)
*A61B 8/08* (2006.01)

(56) References Cited

U.S. PATENT DOCUMENTS

| | | |
|---|---|---|
| 6,283,919 B1 | 9/2001 | Averkiou |
| 6,458,083 B1 | 10/2002 | Averkiou |
| 6,623,432 B2 | 9/2003 | Averkiou |
| 7,547,283 B2 | 6/2009 | Frederickson |
| 2004/0230124 A1 | 11/2004 | Querfurth |
| 2007/0016046 A1 | 1/2007 | Mozayeni |
| 2011/0137182 A1 | 6/2011 | Bellezza |
| 2016/0256130 A1 | 9/2016 | Hamilton |

OTHER PUBLICATIONS

Gu, X. et al., "A novel instantaneous phase difference estimator: piecewise maximum cross-correlation function", IEEE, China, Jun. 2011.

Liu, H. et al., "The application of non-linear flow resistance in cerebral artery: compared with windkessel model based on genetic algorithm", IEEE, 2019.

Kashif, F. et al., "Model-based noninvasive estimation of intracranial pressure from cerebral blood flow velocity and arterial pressure", Sci Transl Med. 2012.

INTRACRANIAL BLOOD PRESSURE ESTIMATION METHOD AND DEVICE

This application is the U.S. National Phase application under 35 U.S.C. § 371 of International Application No. PCT/EP2020/059332, filed on 2 Apr. 2020, which claims the benefit of U.S. Provisional Application Ser. No. 62/832,077, filed 10 Apr. 2019. These applications are hereby incorporated by reference herein.

FIELD OF THE INVENTION

The present invention relates to a method for deriving an estimate of intracranial blood pressure non-invasively, and a device for the same.

BACKGROUND OF THE INVENTION

Intracranial Pressure (ICP) is the pressure inside the skull and thus in the brain tissue and cerebrospinal fluid (CSF). The standard units of measurement are millimeters of mercury (mmHg). For a typical adult human in a supine position, typically values may vary anywhere between around 7-15 mmHg. The body has various mechanisms by which it keeps the ICP stable, with CSF pressures varying by about 1 mmHg in normal adults through shifts in production and absorption of CSF.

Changes in ICP can be indicative of various bodily phenomena, events or conditions. CSF pressure for instance has been shown to be altered by intrathoracic pressure fluctuations during coughing (intra-abdominal pressure), Valsalva maneuver, and communication with the vasculature (venous and arterial systems).

ICP has been shown in particular to be an early onset indicator of traumatic brain injury (TBI).

Despite the potential power of using ICP as an indicator of TBI, there is presently no ability to measure it outside of a hospital environment (e.g. in the prehospital setting, for instance at a General Practitioner (GP) Surgery).

Current ICP monitoring methods are highly invasive requiring surgical penetration of the skull to place intraparenchymal or ventricular sensors and are thus restricted to severe cases where monitoring and/or cerebrospinal fluid (CSF) drainage is required.

Intracranial pressure can be measured noninvasively using a method involving transcranial Doppler (TCD) ultrasound and arterial blood pressure measurements. This method is described in the paper: Kashif et al., "Model-based noninvasive estimation of intracranial pressure from cerebral blood flow velocity and arterial pressure", 2012). This method utilizes a known relationship between cerebral blood flow velocity (CBFV) and ICP, reducing the time-dependent cranial volume relationship to a simplified model, analogous to that of the Windkessel model of vascular dynamics (Westerhof et al., "The arterial Windkessel", 2009).

In one study conducted on 37 patients at the Massachusetts Institute of Technology (MIT), this method produced non-invasive intracranial pressure (nICP) estimations with a mean error of 1.6 mmHg and a standard deviation of the error of 7.6 mmHg, compared to invasive ICP.

In the method used, ICP is modeled as the pressure within the brain that limits blood flow in the brain during the systolic and diastolic phases of the cardiac cycle. Over a number of cardiac cycles, ICP can be estimated based on two inputs: cerebrovascular blood flow velocity (CBFV) and arterial blood pressure (ABP).

ABP, traditionally measured with high accuracy and precision with an invasive radial artery catheter, can be estimated non-invasively with a finger-cuff technique. The Nexfin® finger cuff device for example, which operates based on brachial pressure wave analysis, has recently exhibited comparable accuracy and precision in controlled cardiosurgical environments.

A primary limitation of noninvasive blood pressure devices for nICP estimation is that they cannot measure blood pressure within the brain. Acquiring ICP estimation using such devices therefore necessitates modification of the blood pressure waveform in phase and amplitude to estimate the pressure in the brain vessel.

This is illustrated in FIG. 1 which depicts typical blood pressure waveforms measured at different locations in the body. Each waveform shows the blood pressure (y-axis) as a function of time (x-axis) over a single heart cycle. As a reference, signal (h) shows the waveform for blood pressure as measured at the heart, within the Aorta. Signal (a) shows the waveform for blood pressure as measured in the brain, in the middle cerebral artery, the largest artery of the Circle-of-Willis. Signal (b) is the blood pressure waveform for the same cycle as measured at the carotid artery—this is the closest artery to the brain at which blood pressure may typically be directly measured. Signal (c) is the waveform as measured at the brachial artery, and signal (d) the waveform as measured at the radial artery (the typical location for invasive peripheral pressure monitors).

As shown, blood pressure signals for the same heart cycle vary in phase at different measurement locations of the body. This causes problems for accurately measuring blood pressure within the brain, and therefore in accurately estimating intracranial pressure (ICP) non-invasively within the brain. In addition, and more generally, pulse pressure onset time (relative to blood flow onset) is a valuable clinical parameter by itself. For example, pulse pressure onset time within the brain is directly indicative of cerebral autoregulation.

SUMMARY OF THE INVENTION

The invention is defined by the claims.

According to examples in accordance with an aspect of the invention, there is provided a method for deriving an estimation of intracranial blood pressure, comprising:

obtaining a first signal, indicative of cerebral blood vessel wall movement as a function of time; obtaining a second signal, indicative of cerebral blood flow velocity as a function of time; obtaining a third signal, indicative of blood pressure at a location outside of the brain as a function of time, the first, second and third signals corresponding to measurements over the same time period; detecting a phase offset of the second signal with respect to the first; and transforming the third signal by applying to the third signal a phase shift such that the third signal exhibits a phase offset with respect to the second signal of an amount equal to said detected phase offset, to thereby obtain a fourth signal indicative of estimated intracranial blood pressure.

Embodiments of the invention propose an approach to shift the phase of a pressure waveform collected anywhere in the vasculature, to coincide with the true blood pressure at the location where the blood velocity is measured in the brain.

The first signal, indicative of cerebral blood vessel wall movement, provides an indirect indication of changing blood pressure within the artery. The detected phase shift thus gives an indication of a difference (within the brain region) between the onset of systole (or any other reference point within the heart cycle) as reflected in the cerebral blood pressure signal and the onset of systole as reflected in the changing blood flow velocity. By applying this same offset to the blood pressure measurement signal detected outside of the brain, this latter signal can be transformed to more accurately represent the true blood pressure inside the brain (the intracranial blood pressure). In particular, the blood pressure measurement signal is shifted so as to be in (phase) alignment with the wall-movement signal.

The first, second and third signals are periodic signals as a function of time and exhibit a phase.

Intracranial means the space inside the cranium. Cerebral means inside the brain tissue, i.e. of blood vessels inside the brain. The cerebral blood flow velocity means cerebrovascular blood flow velocity.

Detecting the phase offset may mean detecting an offset (e.g. in the time domain) between pre-determined fiducial points in the cycles of each (periodic) signal. This may mean detecting an offset between a first pre-determined (phase) point in the cycle (period) of the second signal and a second pre-determined (phase) point in the cycle (period) of the first signal. The phase offset may be a time difference or time offset. The points may for example be minimum or maximum points, or may be turning points in each cycle. The first pre-determined point may be a point corresponding to onset of a systolic pressure wave through the blood vessel. The second pre-determined point may be a point corresponding to onset of blood flow through the blood vessel.

The transformation of the third signal is to render the third signal (phase) aligned with the first signal.

Advantageously, the method may further comprise deriving an estimation of intracranial pressure based on the fourth signal and the second signal.

Intracranial pressure (ICP) is the pressure inside the skull, and thus in the brain tissue and cerebrospinal fluid (CSF). It can be estimated based on two inputs: cerebral blood flow velocity and arterial blood pressure inside the brain. Hence the second and fourth signals can be used to derive an estimation of intracranial pressure. This will be explained in more detail to follow.

In examples, the first and second signals may be obtained using transcranial Doppler ultrasound data.

Using ultrasound has the advantage that it is non-invasive, and so more convenient for the patient and also safer and simpler than invasive approaches. Doppler ultrasound is limited in the degree of detail it can obtain about blood pressure. Hence, there remains the need for the blood pressure measurement outside the brain region, which is then transformed as outlined above.

A transcranial Doppler ultrasound unit may be used to acquire the ultrasound data.

The first and second signals may be obtained using a spectral Doppler signal, derived from intracranial Doppler ultrasound data, the spectral Doppler signal representative of Doppler velocity as a function of time.

Spectral Doppler is a term of the art, and refers to a Doppler ultrasound approach which represents blood flow measurements in terms of a spectrum of detected flow velocities recorded over time (as opposed to representing the data with images, such as in Color Doppler approaches).

The obtaining the first signal may comprise extracting from the spectral Doppler signal a relative lower frequency signal component.

Additionally or alternatively, the obtaining the second signal may comprise extracting from the spectral Doppler signal a relative higher (Doppler) frequency signal component.

The signal components correspond to detected velocity signal components. Blood vessel wall motion (cyclic dilation and contraction) typically exhibits a relative slower movement than the faster blood flow velocity. Hence, the blood vessel wall motion manifests as a lower (Doppler) frequency component in the Doppler ultrasound signal than does the (faster) blood flow velocity.

According to one or more embodiments, detecting the phase offset may comprise:

detecting a first time point, corresponding to a location of a first defined phase point within a cycle of the first signal, detecting a second time point corresponding to a location of a second defined phase point within a corresponding cycle of the second signal, and deriving a time difference by subtracting the value of the second time point from the value of the first time point.

The time difference may be a negative value in this case.

The first and second defined phase points preferably both correspond to a same point within a single heart cycle of the subject. Advantageously this may be a point corresponding to onset (i.e. beginning) of the systole phase of the heart. This may manifest as a point at which the wall movement starts to increase from zero (or a minimum value), and may manifest as a point at which the blood flow velocity starts to increase from zero (or a minimum value). This may be a minimum point within each cycle of each signal. It may be a turning point within each cycle, for example a minimum turning point.

The corresponding cycle of the second signal means a cycle corresponding to a same heart phase as the cycle of the first signal, for example an immediately temporally adjacent cycle, or temporally corresponding cycle.

The applying the phase shift to the third signal comprises shifting a waveform of the third signal in the time domain such that it exhibits a time offset with respect to the second signal of an amount equal to said derived time difference.

This typically results in a shift of the waveform of the third signal backwards along the time domain.

The first and second signals are obtained from transcranial Doppler ultrasound data, and wherein the method includes receiving intracranial ultrasound data from a transcranial ultrasound transducer unit.

The transducer unit may be an intracranial ultrasound probe.

In cases where ultrasound is used, the method may further comprise applying beamforming to received transcranial ultrasound data in accordance with one or more beamforming settings. A signal analysis procedure may be applied to determine a quality metric of the beamformed data, representative of a quality of the data for deriving flow velocity and/or blood vessel wall motion.

The method may further comprise adjusting the one or more beamforming settings based on the derived quality metric.

Examples in accordance with a further aspect of the invention provide a processing unit for deriving an estimation of intracranial blood pressure, the processing unit configured to:

obtain a first signal, indicative of cerebral blood vessel wall movement as a function of time; obtain a second signal, indicative of cerebral blood flow velocity as a function of time; obtain a third signal, indicative of blood pressure at a location outside of the brain as a function of time, the first, second and third signals corresponding to measurements over the same time period; detect a phase offset of the second signal with respect to the first, and transform the third signal by applying to the third signal a phase shift such that the third signal exhibits a phase offset with respect to the second signal of an amount equal to said detected phase offset, to thereby obtain a fourth signal indicative of estimated intracranial blood pressure.

The processing unit may be operatively coupleable in use with a transcranial ultrasound transducer unit for obtaining from the transducer unit transcranial Doppler ultrasound data, and wherein the first and second signals are obtained using the transcranial Doppler ultrasound data.

The processing unit may control the transducer unit to obtain transcranial ultrasound data, or may receive data from a transducer unit which is independently controlled.

A further aspect of the invention provides an ultrasound system comprising:

a processing unit in accordance with any example or embodiment outlined above or described below, or in accordance with any claim of this application, and a transcranial ultrasound transducer unit, operatively coupled with the processing unit.

The transcranial ultrasound transducer unit may be controlled by the processing unit to acquire transcranial Doppler ultrasound data, and wherein the first and second signals are obtained using the transcranial Doppler ultrasound data.

A further aspect of the invention provides a patient monitor, comprising:

a processing unit in accordance with any example or embodiment outlined above or described below, or in accordance with any claim of this application, or an ultrasound system as set out above or described in any embodiment herein, and the patient monitor communicatively coupled with a blood pressure measurement device, and configured to obtain from said device said third signal, and to communicate said signal to the processing unit for use in deriving said fourth signal.

It is noted that although the above outlined aspects of the invention provide for transformation of the third signal to obtain a signal indicative of cerebral blood pressure, the general concept embodied by the invention may in other aspects have more general application.

According to one or more alternative aspects of the invention for instance, there may be provided a method for deriving phase information (e.g. a phase offset) between (1) onset of blood pressure in a cerebral blood vessel and (2) a detected pressure waveform at a location outside of the brain (elsewhere in the body). This phase information might be used in a number of different ways (e.g. for deriving generalized or specialized transfer functions, phase shift, scalar input to convolutional neural networks to determine ICP or other cerebrovascular quantities). This will be outlined further below.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
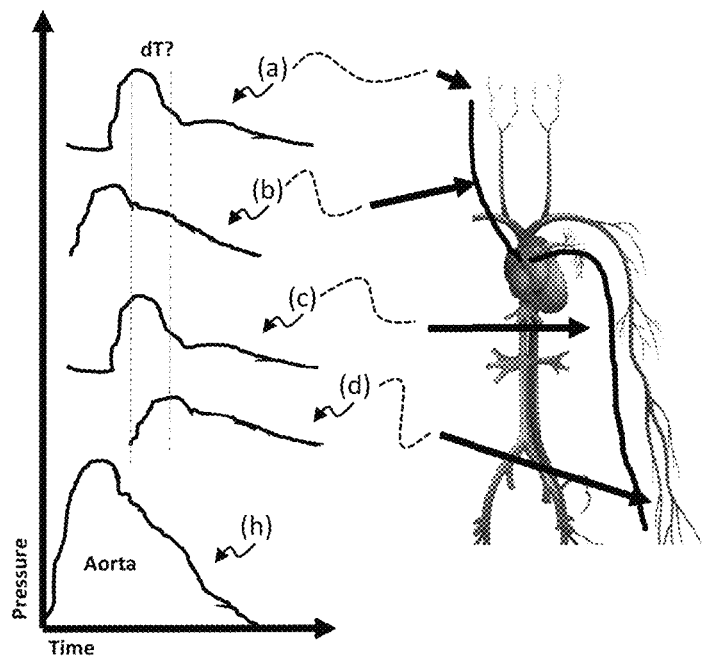
FIG. 1 illustrates blood pressure signals acquired at different locations in the body.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method and device for deriving an estimate of intracranial blood pressure based on motion data for a wall of an intracranial blood vessel, intracranial blood flow velocity, and a blood pressure signal measured at a location outside the brain. The method is based on identifying a time offset between the two intracranial signals (vessel wall movement and vessel blood flow), and then applying this offset to the blood pressure signal acquired from outside the brain.

The wall movement is indirectly indicative of intracranial blood pressure. Hence, the derived offset gives the offset within the brain between the intracranial blood pressure and the intracranial blood flow velocity. Adjusting the external blood pressure signal such that it has the same offset with respect to the intracranial blood flow velocity signal, thus yields a blood pressure signal which is properly temporally synchronized with the true intracranial blood pressure signal. The derived blood pressure signal is rendered aligned (in the time domain) with true intracranial blood pressure.

As discussed above, ICP can be estimated non-invasively. One method is described in detail in the paper: Kashif et al., "Model-based noninvasive estimation of intracranial pressure from cerebral blood flow velocity and arterial pressure", 2012.

In this method for example, ICP is modeled as the pressure that limits blood flow during the systolic and diastolic phases of the cardiac cycle. This model can be used for estimating intracranial pressure noninvasively from arterial blood pressure (ABP) inside the brain and cerebrovascular blood flow velocity (CBFV).

Figure 2:
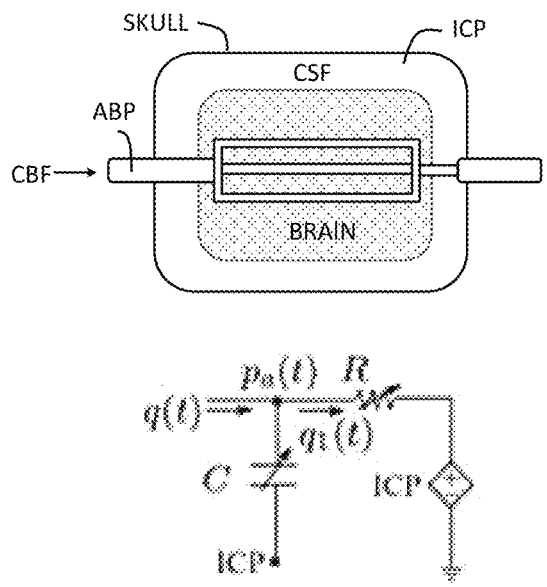
FIG. 2 illustrates an example model for use in deriving estimated intracranial pressure (ICP) non-invasively.

This model can be understood by analogy to an electrical circuit, with a modelled resistance, and a modelled capacitance. This is illustrated in FIG. 2, which schematically depicts a model of the brain and surrounding cerebrospinal fluid (CSF), and the modelled analogous circuit diagram. The capacitance represents a degree of blood retention by the vasculature of the brain each cycle, and the resistance represents a degree of resistance to blood flow through the vasculature, i.e. caused by the flow restriction imposed by the finite diameter blood vessels.

Over a number of cardiac cycles, the 'resistance' (R) and 'capacitance' (C) of this analogous circuit, and the ICP, may be estimated based on two inputs: cerebrovascular blood flow velocity (CBFV) and arterial blood pressure (ABP) within the brain.

However, as noted above, measuring blood pressure directly in the brain (in a non-invasive manner) is not possible with current technology, and hence must be measured outside the brain. However, blood pressure signals vary in phase at different measurement locations of the body. Hence, the measured waveform much be transformed in order to be representative of blood pressure inside the brain, and so yield an accurate estimation of ICP.

A key challenge in this approach is therefore applying a transfer function to shift blood pressure measured outside of the brain (for example in the radial artery) to resemble the pressure at the cerebrovascular artery of interest inside the brain.

Embodiments of the present invention propose an approach to shift the phase of a pressure waveform collected anywhere in the vasculature, to coincide with the pressure where the blood velocity is measured in the brain. This thus enables intravascular blood pressure to be more accurately estimated. Thus, ICP can be measured non-invasively in a more accurate and reliable manner based on this adjusted blood pressure waveform.

This approach offers an advantage over currently used (global) approaches, which assume a constant phase delay between blood pressure signals throughout the body. In fact, the pulse wave velocity is known to vary with changing peripheral resistance, arterial compliance, and other compensatory hemodynamic factors.

In more detail, embodiments of the invention propose to combine blood flow velocity measurements (derived for example from spectral Doppler imaging) with blood vessel motion data (derived for example from tissue Doppler imaging, performed simultaneously) to derive non-invasive intracranial pressure estimations, for example using techniques known in the art.

A key feature according to one set of embodiments, to be described below, is the concurrent use of a low frequency component of an acquired Doppler spectrogram to determine the onset time of systolic blood pressure relative to the blood flow velocity. The low frequency component may represent blood vessel wall motion (indicative of blood pressure changes). The phase difference between the zero crossing of this motion data and the onset of blood flow in the artery (represented by a high frequency component of spectral Doppler data) may be used to shift a pressure waveform collected outside of the brain (e.g. radial artery).

Figure 3:
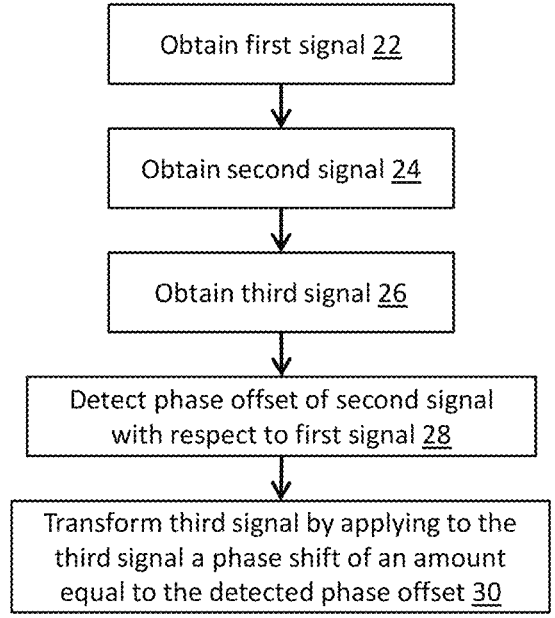
FIG. 3 shows a block diagram of an example method according to one or more embodiments.

A block diagram of one example method according to one or more embodiments of the invention is shown in FIG. 3. The method is for deriving an estimation of intracranial blood pressure.

In brief, the method 20 comprises obtaining three different signals: obtaining 22 a first signal, indicative of cerebral blood vessel wall movement as a function of time; obtaining 24 a second signal, indicative of cerebral blood flow velocity as a function of time; and obtaining 26 a third signal, indicative of blood pressure at a location outside of the brain as a function of time. The second signal may be indicative of cerebral blood flow velocity.

The first, second and third signals correspond to measurements taken over the same time period.

The signals may be obtained directly from measurement devices in use on a subject's body. They may be obtained from a patient monitor at which relevant measurement data is being collected. They may be obtained from a local or remote data store. These represent examples only, and the signals may be obtained from any other source, either in real time with measurement or at a time subsequent to measurements being performed.

The method 20 further comprises detecting 28 a phase offset of the second signal with respect to the first.

The method 20 further comprises transforming 30 the third signal by applying to the third signal a phase shift of an amount equal to the detected phase offset, to thereby obtain a fourth signal indicative of estimated intracranial blood pressure.

Detecting the phase offset may mean detecting an offset (e.g. in the time domain) between pre-determined fiducial points in the cycles of each (periodic) signal. This may mean detecting an offset between a first pre-determined (phase) point in the cycle (period) of the second signal and a second pre-determined (phase) point in the cycle (period) of the first signal. The phase offset may be a time difference or time offset. The points may for example be minimum or maximum points, or may be turning points in each cycle.

Figure 4A:
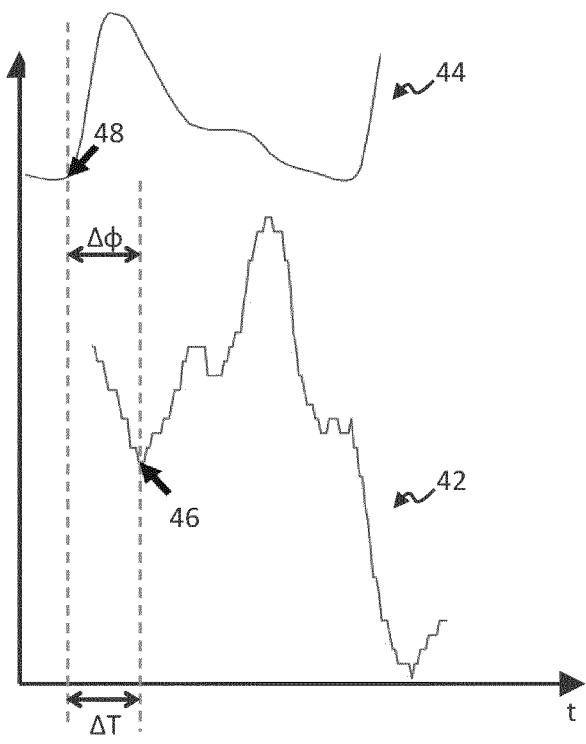
FIG. 4A illustrates detection of a phase offset between an intracranial blood flow velocity signal and a intracranial blood vessel wall movement signal.

FIG. 4A illustrates an example phase offset detection procedure.

FIG. 4A shows an example first signal 42 indicative of cerebral blood vessel wall movement as a function of time, and an example second signal 44 indicative of cerebral blood flow velocity as a function of time. FIG. 4 illustrates that there is a phase offset $\Delta\phi$ between a first pre-determined point 46 in the cycle of the first signal 42 and a second predetermined point 48 in the cycle of the second signal 44.

The first and second phase points 46, 48 are each minimum points in the respective signals. The first 46 and second 48 defined phase points both correspond to a same point within a single heart cycle of the subject. In this example, this point is a point corresponding to onset (i.e. beginning) of the systole phase of the heart. The first pre-defined point 46 is hence a point corresponding to onset of a systolic pressure wave through the measured cerebral blood vessel. The second pre-defined point 48 is a point corresponding to onset of blood flow through the same cerebral blood vessel.

In more detail, detecting the phase offset may comprise:

detecting a first time point, T1, corresponding to a location of a first defined phase point 46 within a cycle of the first signal 42, detecting a second time point, T2, corresponding to a location of a second defined phase point 48 within a corresponding cycle of the second signal 44, and deriving a time difference, $\Delta T$, between the value of the second time point, T2, and the value of the first time point, T1.

Hence here the phase difference is equated with a time difference, so that the phase difference is time difference $\Delta T$.

Figure 4B:
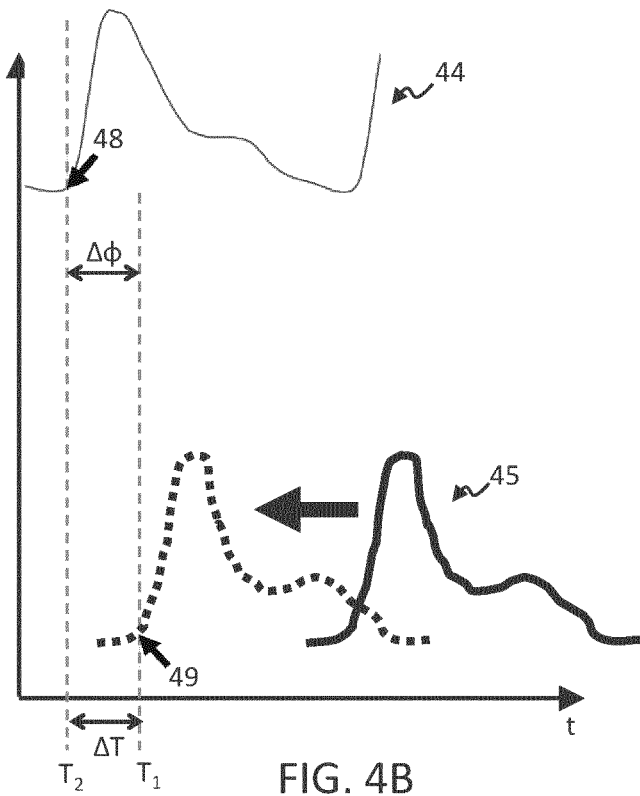
FIG. 4B illustrates transformation of a non-cerebral blood pressure signal by application of a phase shift in the time domain, the phase shift based on the detected phase offset of FIG. 4A.

FIG. 4B illustrates an example transformation of the third signal 45 (indicative of blood pressure at a location outside of the brain as a function of time) based on the derived phase offset (or time difference ΔT) between the second signal 44 and the first signal 42.

As shown in FIG. 4B, the transformation comprises applying a phase shift to the third signal 45, which manifests as a shift in a waveform of the third signal (backward) in the time domain, t. As shown, the waveform of third signal 45 is shifted in the time domain such that, after the shift, it exhibits a time offset with respect to the second signal 44 of an amount equal to said derived time difference, ΔT.

In particular, the third signal waveform 45 is shifted so that a defined phase point 49 in the third signal (corresponding to the same point in the heart cycle as point 46 in the first (wall movement) signal) is rendered offset with respect to the defined phase point 48 of the second signal 44 by a time difference of ΔT (or, equivalently, a phase offset of Δϕ). The defined phase point 49 of the third signal corresponds in this example to onset of the systole phase of the heart, i.e. onset of the (systolic) pressure wave represented by the third signal 45. However, in other examples, any other point in the waveform (the heart cycle) may be used.

According to a preferred set of embodiments, the first and second signals are obtained using transcranial Doppler ultrasound data. The signals may be obtained using a transcranial ultrasound transducer unit, e.g. a transcranial ultrasound probe.

Figure 5:
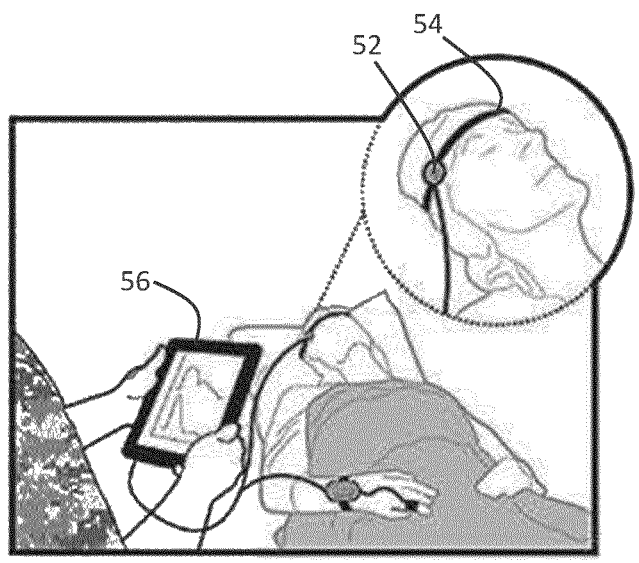
FIG. 5 depicts an example transcranial ultrasound probe in use.

An example transcranial ultrasound probe 52, mounted in use on a subject's head is shown in FIG. 5. The ultrasound probe preferably comprises an ultrasound transducer array to permit beamforming. FIG. 5 also illustrates simultaneous collection of a blood pressure measurement signal (a third signal according to the method outline above) at a location outside the brain, in particular the finger.

The ultrasound probe may be manipulable by a user along the surface of the head, for instance anterior to the ear. This may enable volumetric ultrasound data acquisition. Manipulation may be via adjustment of the probe to different positions by release and tightening of a head band or frame holding the probe to the subject's head.

An example patient monitor device 56 is also shown at which the collected data is displayed to an operator (e.g. a clinician). The patient monitor in this case is shown as a tablet computer device. However, any form of patient monitor might alternatively be used, including a trolley-type patient monitor with a processor, arranged to perform the steps of the described herein method, and display unit for instance.

In a preferred set of embodiments, the first and second signals may be obtained using a spectral Doppler signal, derived from intracranial Doppler ultrasound data, the spectral Doppler signal representative of measured Doppler velocity as a function of time.

The obtaining the first signal may then comprise extracting from the spectral Doppler signal a relative lower frequency signal component.

The obtaining the second signal may comprise extracting from the spectral Doppler signal a relative higher frequency signal component.

For example, spectral Doppler ultrasound data may be collected using an ultrasound system operating in spectral Doppler mode. This may be arranged or controlled to focus ultrasound pulses toward a cranial vessel of interest. Methods for localizing a desired blood vessel will be described further below.

This ultrasound system may then for example send the acquired beamformed RF ultrasound data to a signal processing unit for spectral analysis.

Blood vessel motion information may be derived from the low frequency content of the spectral Doppler signal. A low pass filter may be applied to the ultrasound data to obtain this low frequency component. From the blood vessel motion information, the mechanical response of the blood vessel to the propagating blood pressure wave may be estimated. When the blood pressure wave arrives during the systolic phase of the heart cycle, the vessel wall feels a higher transmural pressure and dilates radially. The component of this relatively slow wall velocity that is directed towards the ultrasound transducer manifests as low frequency content in the Doppler spectrogram.

Figure 6:
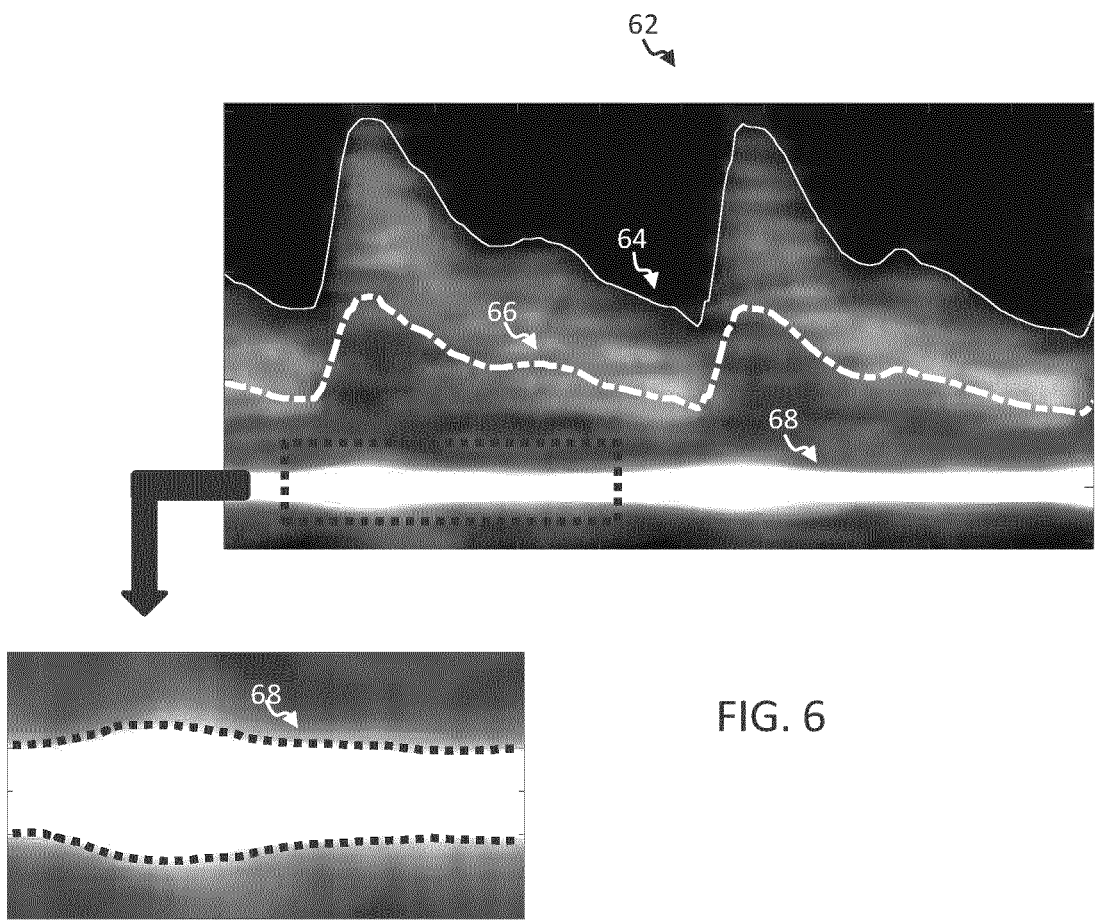
FIG. 6 depicts an example Doppler spectrogram and extracted blood vessel wall movement signal obtained in accordance with one or more embodiments.

This is illustrated by FIG. 6, which shows a graph representing an example Doppler spectrogram 62 for a patient having suffered a traumatic brain injury. The y-axis represents blood flow velocity, the x-axis represents time. The higher Doppler frequency component (higher velocity component) is indicated by arrow 64. This corresponds to the blood flow velocity. The lower frequency component is indicated by arrow 68. This corresponds to the blood vessel wall movement (dilation and contraction).

The envelope of the blood flow velocity signal is shown at arrow 64. The average of the blood flow velocity is shown at arrow 66. The envelope of the blood vessel wall motion signal is shown at arrow 68. This part of the signal is shown in larger form beneath the main spectrogram, with the y-axis representing velocity (units: cm/s) and the x-axis representing time.

The cerebral flow velocity mean (shown by dotted line indicated by arrow 66) and also the maximum may be extracted from the high frequency content. Peak detection may be applied to the wall velocity envelope 68, and this used to determine the blood pressure onset in the vessel-of-interest. This maximum point may be used as the phase point with respect to which the phase offset discussed above is detected, and the phase shift procedure may then be applied to the blood pressure signal collected elsewhere in the body based on this.

Figure 7:
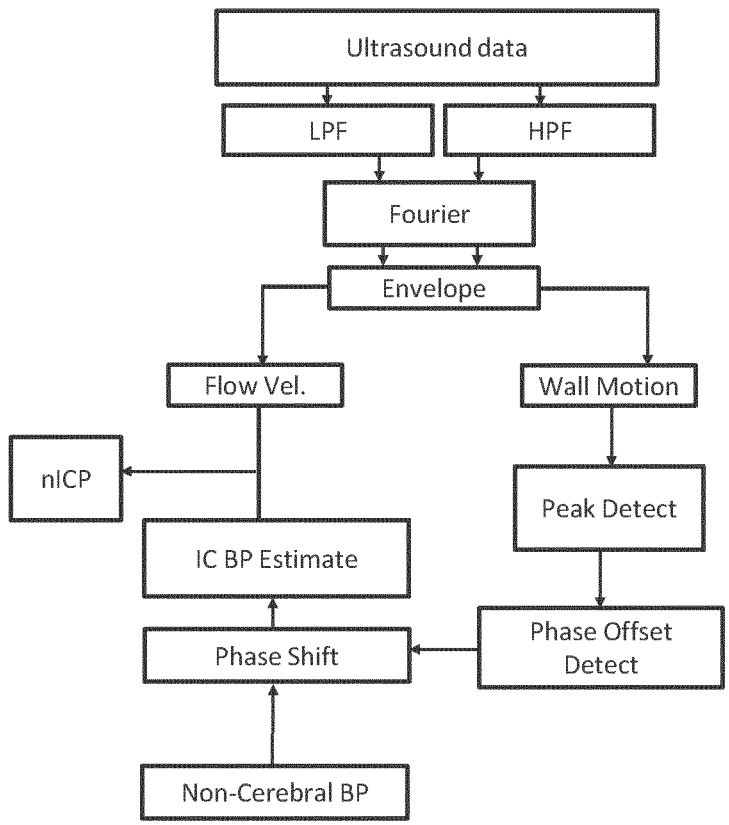
FIG. 7 shows a further example method according to one or more embodiments.

FIG. 7 shows a block diagram outlining the steps of an example method including the signal processing steps for extracting the relevant signal components from a spectral Doppler Ultrasound signal.

The shown method comprises receiving demodulated ultrasound data, for example from an ultrasound system or from a local or remote data-store. The method next comprises applying a low pass filter (LPF) to the received data, and also applying a high pass filter (HPF) to the data to extract the low and high frequency components from the raw ultrasound data. The high and low pass filters are applied separately to different respective copies of the ultrasound data (as opposed to in sequence). This results in two sets of output data: a high-pass filtered data set and a low-pass filtered data set.

A Fourier transform ('Fourier') is then applied to each dataset to derive a frequency spectrum representation of the data (i.e. a Doppler spectrogram).

In advantageous examples, a Fourier transform is calculated separately for the low pass and high pass filtered signals respectively. For example, the Fourier analysis step may comprise calculating a short time complex Fourier transform (spectrogram) separately for the low pass and high pass filtered data. It is known that in general, the dynamics of the these two signals are quite different (one exhibits high velocity, while the other exhibits low velocity, and one exhibits slow changes while the other exhibits more rapid changes. Thus it is advantageous to select sampling frequencies (e.g. resampling/decimation), window lengths (thus determining frequency bin size and spectral bleed), and window overlaps tailored to each different signal.

Envelopes of the low and high frequency signal components (the wall motion and the blood flow components) are then detected and extracted to provide respectively the first and second signals of the method of FIG. 3 described above.

The low frequency wall motion envelope signal is processed and peak detection applied. At least one of the detected peaks (for instance the highest peak, or the first peak following an initial rise from zero) is used as the basis for detecting a phase offset between the blood flow velocity envelope signal and the wall motion envelope signal. For instance a phase offset (e.g. a time offset) between corresponding peaks in the two signals may be detected.

A phase shift is then applied to a non-cerebral blood pressure (BP) signal obtained from elsewhere in the body, this phase shift being based on the detected phase offset. The signal may be shifted in the time domain so as to have the same phase offset with respect to the blood flow velocity signal as the wall motion signal for example.

The phase shift of the non-cerebral BP signal directly yields a signal indicative of an estimated intracerebral blood pressure (IC BP) signal (a fourth signal according to the method of FIG. 3 discussed above).

Optionally, from this IC BP estimated signal and the blood flow velocity signal already extracted, a (non-invasive) estimate of the intracranial pressure (nICP) may be obtained. A method for deriving an ICP estimate from these inputs has been described above.

According to any embodiment, the method 20 for estimating intracranial blood pressure may comprise applying beamforming to received transcranial ultrasound data in accordance with one or more beamforming settings, and applying a signal analysis procedure to determine a quality metric of the beamformed data, representative of a quality of the data for deriving flow velocity and/or blood vessel wall motion.

The beamforming settings may include, by way of example, one or more of: focal location, focal gain, apodization. The beamforming settings may include a steering direction of the beamformed beam, i.e. a target location of the beamformed signal.

The quality metric may comprise a strength of the received signal or a strength of one or both of the extracted flow velocity and wall motion signals.

For example, the quality metric may represent a sufficiency of the current beamforming parameters for estimating vessel wall motion information and/or for detecting blood flow velocity information.

The method may further include, responsive to this quality determination, adjusting the one or more beamforming settings based on the derived quality metric.

The settings may be adjusted so as to acquire data with a higher quality metric.

The adjustment may comprise adjusting a steering direction of a beamformed beam to target a different location within the brain.

Optimal beamforming parameters for optimal blood flow velocity and vessel wall motion information may be determined. The optimal parameters may mean those that maximize a signal strength for the relevant signal component for instance, or provide a signal strength exceeding a pre-defined threshold for instance. The determined optimal parameters or settings may then be applied to the ultrasound system.

Identifying the optimal beamforming settings may comprise a procedure of trialing different beamforming settings and detecting a quality metric of the signals obtained with each.

The beamforming settings may include a directionality of the ultrasound beam, i.e. a target focus of the ultrasound signals. Different target locations along one or more cranial blood vessels may be trialed to determine an optimum focus location for the ultrasound beam.

The procedure of adjusting the beamforming settings may be combined with a live color-Doppler or power-Doppler image generation and analysis, to determine an appropriate vessel search path along which to trial for different possible focus locations for the ultrasound beam.

Figure 8:
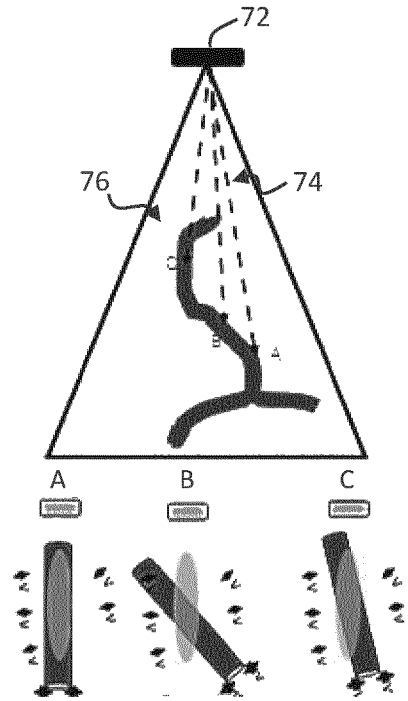
FIG. 8 illustrates a trialing procedure for identifying an optimal ultrasound target location for obtaining blood flow velocity and vessel wall movement data.

FIG. 8 schematically illustrates a trialing procedure for determining an optimal target location (i.e. optimum beam directionality) for the generated ultrasound beam. The figure depicts an example ultrasound transducer array 72, and shows various trial beams 74 which may be generated throughout the trial procedure. The beams are focused toward different target locations, A, B and C, located at different points along a set of cerebral blood vessels (indicated generally by arrow 76).

FIG. 8 (bottom) further schematically depicts the incident directionality of each of the beams on the respective target blood vessel. The view shown is along the direction of the incoming beam, i.e. a cross-sectional view across a plane perpendicular to the beam direction.

For target location A, the strength of the obtained blood flow velocity signal zero because the incident beam is oriented parallel to the direction of the blood flow (parallel the longitudinal direction of the target blood vessel). This results in a very low (e.g. zero) quality metric for the beamforming settings having the beam focused at location A.

For target location B, the strength of the blood flow signal is high, because the incident beam extends transverse the direction of the blood flow. A transverse oriented beam is necessary to measure the blood flow travelling parallel to the length of the blood vessel. The quality metric is hence high.

For target location C, the signal strength is low because the incident beam is oriented at only a small angle with respect to the blood flow direction (i.e. at only a shallow transverse angle). Hence, the quality metric is low.

The trialing procedure of different locations along the cerebral vasculature may be informed by a pre-determined map of the vasculature, allowing different locations to be efficiently identified and focused toward.

Alternatively, the ultrasound system may simply beamform ultrasound signals to various positions in ultrasound space to determine an optimal target location. This process may employ hydrophone measurements.

Above have been described various embodiments of a method for estimating intracerebral blood pressure.

In a further aspect of the invention, there may be provided a processing unit configured to perform a method according to one or more of the embodiments described above or as defined in any claim of this application.

The processing unit can be implemented in numerous ways, with software and/or hardware, to perform the various functions required. The processing unit may embody or comprise a processor. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processing unit may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

A further aspect of the invention may provide an ultrasound system comprising: a processing unit as described above, and a transcranial ultrasound transducer unit, operatively coupled with the processing unit, and operable to supply to the processing unit Doppler ultrasound data. The processing unit may include means for processing the data to extract the first, second and third signals defined above, and for performing the phase shift procedure to derive the fourth signal defined above. Separate processing elements may alternatively be provided to process the ultrasound data to derive the first, second and third signals.

A further aspect of the invention provides a patient monitor, comprising:

a processing unit as described above, and the patient monitor communicatively coupled with a blood pressure measurement device, and configured to obtain 26 from said device said third signal, and to communicate said signal to the processing unit for use in deriving said fourth signal.

In particular embodiments, there may be provided a system comprising: a transcranial ultrasound probe, and an ultrasound system configured to drive the ultrasound probe in conventional spectral Doppler mode to acquire ultrasound data representative of the brain region. The system further includes a signal processing unit configured to receive Doppler ultrasound data from the ultrasound system (for instance in-phase/quadrature data) and to extract relative high and low Doppler frequency signal components from the data. The high and low frequency signals are representative blood and tissue velocities respectively. The signal processing unit may further determine phase information indicative of the onset time of blood pressure changes relative to the blood velocity.

A bridge unit, e.g. a processor, may be further included, configured to receive the blood flow velocity and phase information from the ultrasound system, and receive the blood pressure information from the patient monitor, and to compute from these inputs intracranial pressure noninvasively.

It is noted that although the above outlined aspects of the invention provide for transformation of the third signal to obtain a signal indicative of cerebral blood pressure, the general concept embodied by the invention may in other aspects have more general application. In particular, the pulse pressure onset time within the brain is a valuable clinical parameter in itself.

According to one or more alternative aspects of the invention for instance, there may be provided a method for deriving phase information (e.g. a phase offset) between (1) onset of blood pressure in a cerebral blood vessel and (2) a detected pressure waveform at a location outside of the brain (elsewhere in the body).

By way of example, alternative aspects of the invention may provide a method for deriving an estimation of intracranial blood pressure, comprising: obtaining a first signal, indicative of cerebral blood vessel wall movement as a function of time; obtaining a second signal, indicative of cerebral blood flow velocity as a function of time; obtaining a third signal, indicative of blood pressure at a location outside of the brain as a function of time, the first, second and third signals corresponding to measurements over the same time period.

The method may then further comprise detecting a phase offset of the second signal with respect to the first. This phase offset may then be used in different ways. For instance, this parameter is directly indicative of cerebral autoregulation.

Additionally or alternatively, the method may then further comprise detecting a phase offset of the third signal with respect to the second. This phase information might be used in a number of different ways (e.g. for deriving generalized or specialized transfer functions, or as a scalar input to convolutional neural networks to determine ICP or other cerebrovascular quantities).

As discussed above, certain embodiments of the invention include means for acquiring Doppler ultrasound data, and for performing beamforming.

These functions may be facilitated with an ultrasound system having an ultrasound transducer array.

Figure 9:
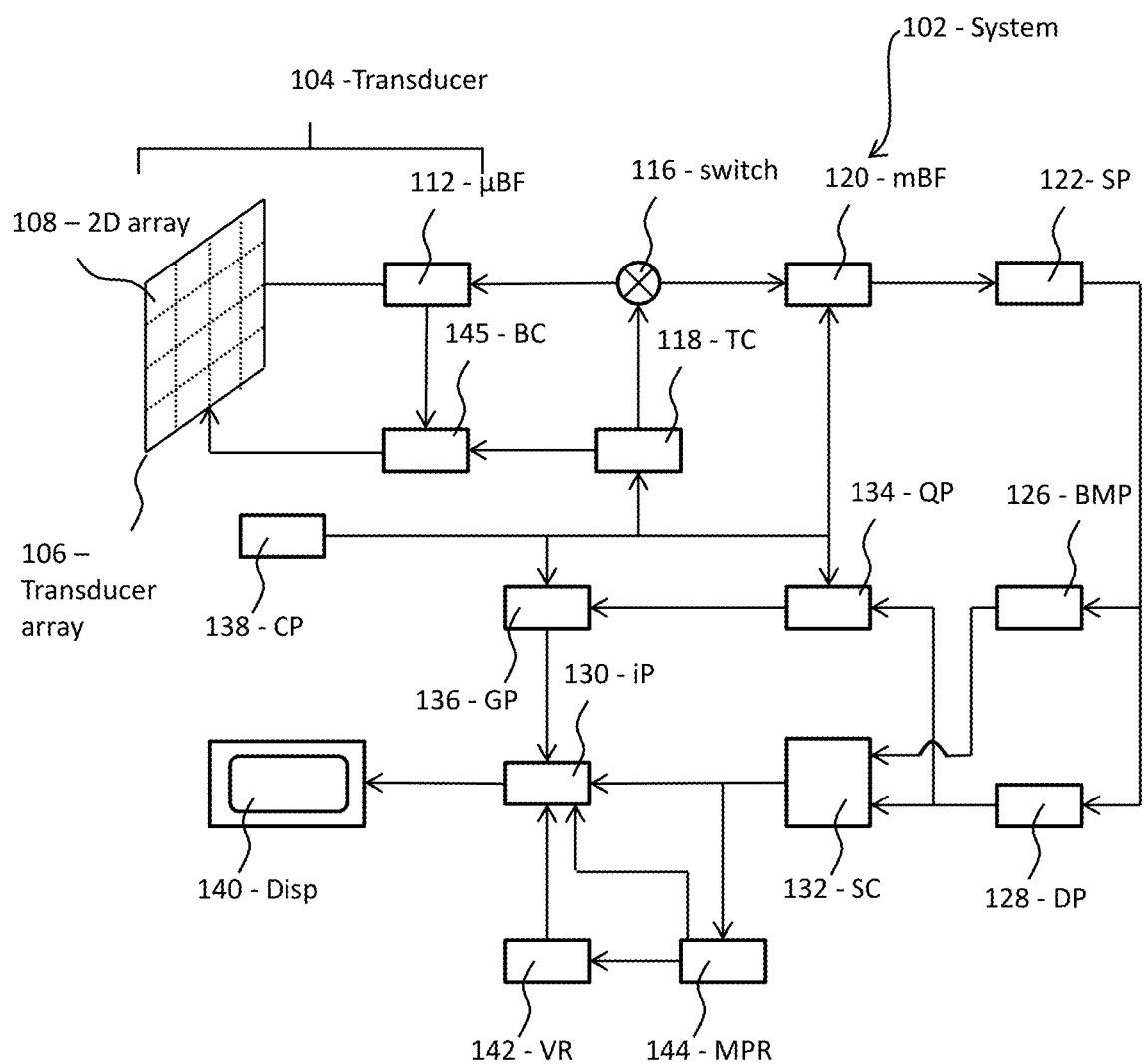
FIG. 9 depicts an example ultrasound system as may be used for acquiring and processing ultrasound data for use in one or more embodiments.

An example ultrasound system, as may be used to facilitate acquisition and processing of the ultrasound data, will now be described with reference to FIG. 9.

The system comprises an array transducer probe 104 which has a transducer array 106 for transmitting ultrasound waves and receiving echo information. The transducer array 106 may comprise CMUT transducers; piezoelectric transducers, formed of materials such as PZT or PVDF; or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is in general entirely optional. Further, the system includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of a user interface or control panel 138. The controller 118 can include transmission circuitry arranged to drive the transducer elements of the array 106 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 9 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 128 processes temporally distinct signals arising from tissue movement and blood flow for the detection of moving substances, such as the flow of blood cells in the image field. The Doppler processor 128 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for optional display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made.

Output data from the quantification processor may be coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor may receive input from a user interface 138. Such a user interface may also be coupled to the transmit controller 118 to control the generation of ultrasound signals from the transducer array 108 and hence the images produced by the transducer array and the ultrasound system. The transmit control function of the controller 118 is only one of the functions performed. The controller 118 also takes account of the mode of operation and the corresponding required transmitter configuration and band-pass configuration in the receiver analog to digital converter. The controller 118 can be a state machine with fixed states.

The user interface may also be coupled to the multi-planar reformatter 144 for selection and control of the planes of multiple multi-planar reformatted (MPR) images which may be used to perform quantified measures in the image field of the MPR images.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for deriving an estimation of intracranial blood pressure via an ultrasound system, wherein the ultrasound system includes an ultrasound transducer and a processor, comprising:
   obtaining a first signal from the ultrasound transducer; indicative of cerebral blood vessel wall movement as a function of time;
   obtaining a second signal from the ultrasound transducer; indicative of cerebral blood flow velocity as a function of time;
   obtaining a third signal, indicative of blood pressure at a location outside of the brain as a function of time,
   the first, second and third signals corresponding to measurements over the same time period;
   detecting a phase offset of the second signal with respect to the first; and
   transforming the third signal by applying to the third signal a phase shift such that the third signal exhibits a phase offset with respect to the second signal of an amount equal to said detected phase offset, to thereby obtain a fourth signal indicative of estimated intracranial blood pressure.

2. The method as claimed in claim 1, wherein the method further comprises deriving an estimation of intracranial pressure based on the fourth signal and the second signal.

3. The method as claimed in claim 1, wherein the first and second signals comprise transcranial Doppler ultrasound data.

4. The method as claimed in claim 3, wherein the first and second signals comprise a spectral Doppler signal, derived from intracranial Doppler ultrasound data, the spectral Doppler signal representative of Doppler velocity as a function of time.

5. The method as claimed in claim 4, wherein:
   the obtaining the first signal comprises extracting from the spectral Doppler signal a relative lower frequency signal component; and/or
   the obtaining the second signal comprises extracting from the spectral Doppler signal a relative higher frequency signal component.

6. The method as claimed in claim 1, wherein the detecting the phase offset comprises:
   detecting a first time point, corresponding to a location of a first defined phase point within a cycle of the first signal;
   detecting a second time point corresponding to a location of a second defined phase point within a corresponding cycle of the second signal; and
   deriving a time difference by subtracting the value of the second time point from the value of the first time point.

7. The method as claimed in claim 6, wherein the applying the phase shift to the third signal comprises shifting a waveform of the third signal in the time domain such that it exhibits a time offset with respect to the second signal of an amount equal to said derived time difference.

8. The method as claimed in claim 1, wherein the transducer is a transcranial ultrasound transducer.

9. The method as claimed in claim 3, further comprising applying beamforming to received transcranial ultrasound data in accordance with one or more beamforming settings, and applying a signal analysis procedure to determine a quality metric of the beamformed data, representative of a quality of the data for deriving flow velocity and/or blood vessel wall motion.

10. The method as claimed in claim 9, further comprising adjusting the one or more beamforming settings based on the derived quality metric.

11. A processor for deriving an estimation of intracranial blood pressure, the processor operatively coupled to an ultrasound transducer, wherein the processor is configured to:
   obtain a first signal via the ultrasound transducer, indicative of cerebral blood vessel wall movement as a function of time;
   obtain a second signal via the ultrasound transducer, indicative of cerebral blood flow velocity as a function of time;
   obtain a third signal, indicative of blood pressure at a location outside of the brain as a function of time;
   the first, second and third signals corresponding to measurements over the same time period;
   detect a phase offset of the second signal with respect to the first, and
   transform the third signal by applying to the third signal a phase shift such that the third signal exhibits a phase offset with respect to the second signal of an amount equal to said detected phase offset, to thereby obtain a fourth signal indicative of estimated intracranial blood pressure.

12. The processor as claimed in claim 11, wherein the comprise transcranial Doppler ultrasound data received via the transducer.

13. The ultrasound system comprising:
   a transcranial ultrasound transducer; and
   a processor configured to:
      obtain a first signal from the transducer, indicative of cerebral blood vessel wall movement as a function of time;
      obtain a second signal from the transducer, indicative of cerebral blood flow velocity as a function of time;
      obtain a third signal indicative of blood pressure at a location outside of the brain as a function of time;
      the first, second and third signals corresponding to measurements over the same time period;
      detect a phase offset of the second signal with respect to the first, and
      transform the third signal by applying to the third signal a phase shift such that the third signal exhibits a phase offset with respect to the second signal of an amount equal to said detected phase offset, to thereby obtain a fourth signal indicative of estimated intracranial blood pressure.

14. A patient monitoring system, comprising:
a blood pressure measurement device;
a processor configured to:
- obtain a first signal via an ultrasound transducer, indicative of cerebral blood vessel wall movement as a function of time;
- obtain a second signal via the ultrasound transducer indicative of cerebral blood flow velocity as a function of time;
- obtain a third signal via the blood pressure measurement device, indicative of blood pressure at a location outside of the brain as a function of time;
- the first second and third signals corresponding to measurements over the same time period;
- detect a phase offset of the second signal with respect to the first, and
- transform the third signal by applying to the third signal a phase shift such that the third signal exhibits a phase offset with respect to the second signal of an amount equal to said detected phase offset, to thereby obtain a fourth signal indicative of estimated intracranial blood pressure.

15. The patient monitoring system of claim 14, wherein the blood pressure measurement device comprises a non-invasive blood pressure measurement device.

16. The patient monitoring system of claim 15, wherein the non-invasive blood pressure measurement device comprises at least one of: a finger cuff device, an arm cuff device, an alar sensor.

17. The method of claim 11, wherein the fourth signal is obtained by transformation of the third signal in real time as the first, second and third signals are obtained.

18. The processor of claim 11, wherein the fourth signal is obtained by transformation of the third signal in real time as the first, second and third signals are obtained.

19. The system of claim 13, wherein the fourth signal is obtained by transformation of the third signal in real time as the first, second and third signals are obtained.

20. Them patient monitoring system of claim 14, wherein the fourth signal is obtained by transformation of the third signal in real time as the first, second and third signals are obtained.

* * * * *